(12) United States Patent
Kim et al.

(10) Patent No.: US 8,691,500 B2
(45) Date of Patent: Apr. 8, 2014

(54) DEVICE AND METHOD FOR DETECTING BIOMOLECULE

(75) Inventors: Sang Kyung Kim, Seoul (KR); Kyoungja Woo, Seoul (KR); Yu Ri Choi, Bucheon-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/560,285

(22) Filed: Jul. 27, 2012

(65) Prior Publication Data

US 2013/0029320 A1 Jan. 31, 2013

(30) Foreign Application Priority Data

Jul. 29, 2011 (KR) .................. 10-2011-0075663
Sep. 9, 2011 (KR) .................. 10-2011-0091957

(51) Int. Cl.
*C12Q 1/68* (2006.01)
*C07H 21/04* (2006.01)
*C12M 1/34* (2006.01)
*G01N 21/64* (2006.01)

(52) U.S. Cl.
USPC .............. 435/4; 435/6.1; 435/7.1; 435/283.1; 536/23.1; 536/24.5

(58) Field of Classification Search
None
See application file for complete search history.

(56) References Cited

U.S. PATENT DOCUMENTS

| | | | |
|---|---|---|---|
| 2005/0130167 A1* | 6/2005 | Bao et al. ....................... | 435/6 |
| 2006/0014172 A1 | 1/2006 | Muller et al. | |
| 2006/0245971 A1* | 11/2006 | Burns et al. ..................... | 422/58 |
| 2006/0257915 A1 | 11/2006 | Bruno et al. | |
| 2006/0257958 A1 | 11/2006 | Bruno | |
| 2008/0124779 A1* | 5/2008 | Oh et al. ..................... | 435/173.9 |
| 2010/0129808 A1* | 5/2010 | Mirkin et al. ..................... | 435/6 |
| 2011/0065086 A1 | 3/2011 | Bruno | |

FOREIGN PATENT DOCUMENTS

| | | |
|---|---|---|
| KR | 10-2008-0084029 | 9/2008 |
| KR | 10-2008-0100771 | 11/2008 |
| KR | 10-2011-0055930 | 5/2011 |

OTHER PUBLICATIONS

Shawn P. Mulvaney et al., "Incorporating fluorescent dyes and quantum dots into magnetic microbeads for immunoassays", BioImaging Short Technical Report, BioTechniques, 2004, vol. 36, No. 4, pp. 602-609.

(Continued)

*Primary Examiner* — Betty Forman
(74) *Attorney, Agent, or Firm* — Staas & Halsey LLP

(57) ABSTRACT

Disclosed are a method for detecting a biomolecule including: immobilizing a nucleic acid aptamer capable of specifically binding to a biomolecule to be detected on the surface of a bead on which fluorophores are arranged; hybridizing the nucleic acid aptamer with a guard nucleic acid (g-nucleic acid) labeled with a quencher to quench fluorescence; and reacting a sample including the biomolecule to be detected with the nucleic acid aptamer and detecting a fluorescence signal emitted as the biomolecule binds with the nucleic acid aptamer and the g-nucleic acid labeled with the quencher is separated, and a device for detecting a biomolecule for conducting the detection method. The present disclosure allows for effective, convenient and fast detection of the biomolecule to be detected, enables quantitative analysis, and enables detection of even a trace amount of sample.

7 Claims, 10 Drawing Sheets

(56) References Cited

OTHER PUBLICATIONS

Myungje Cho et al., "Facile Synthesis and optical properties of colloidal silica microspheres encapsulating a quantum dot layer", The Royal Society of Chemistry, 2010, 46, pp. 5584-5586.

Yolanda H. Tennico et al., "On-Chip Aptamer-Based Sandwich Assay for Thrombin Detection Employing Magnetic Beads and Quantum Dots" Analytical Chemistry, vol. 82, No. 13, Jul. 1, 2010, pp. 5591-5597.

J. Bruno et al., "Plastic-Adherent DNA Aptamer-Magnetic Bead and Quantum Dot Sandwich Assay for Campylobacter Detection" Journal of Fluorescence 19, 2009, pp. 427-435.

M. Levy et al., "Quantum-Dot Aptamer Beacons for the Detection of Proteins", ChemBioChem 2005, 6, pp. 2163-2166.

J. Krishnan et al., "Rapid microfluidic separation of magnetic beads through dielectrophoresis and magnetophoresis", Electrophoresis 2009, 30, pp. 1457-1463.

\* cited by examiner

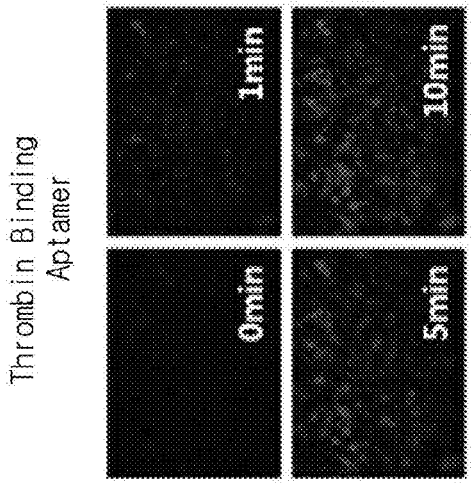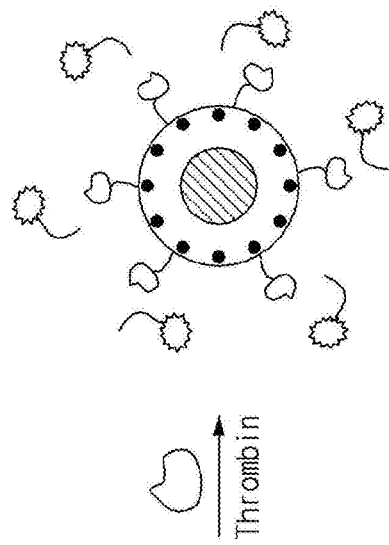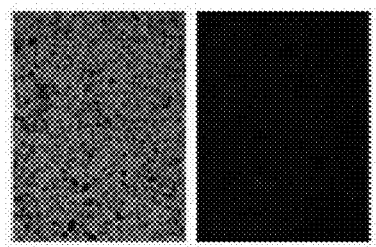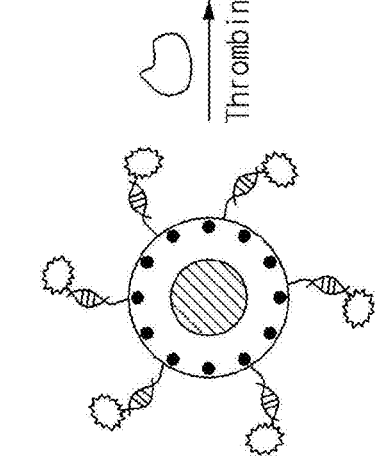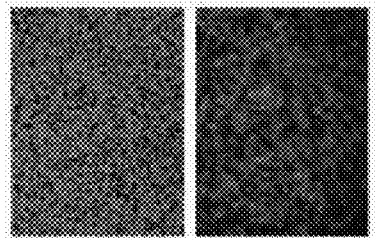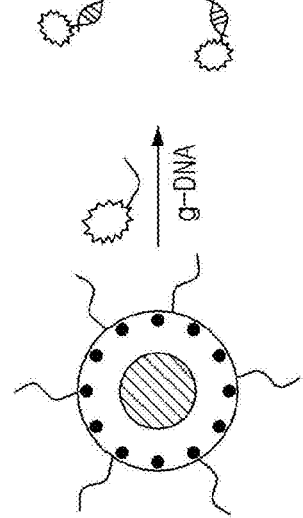

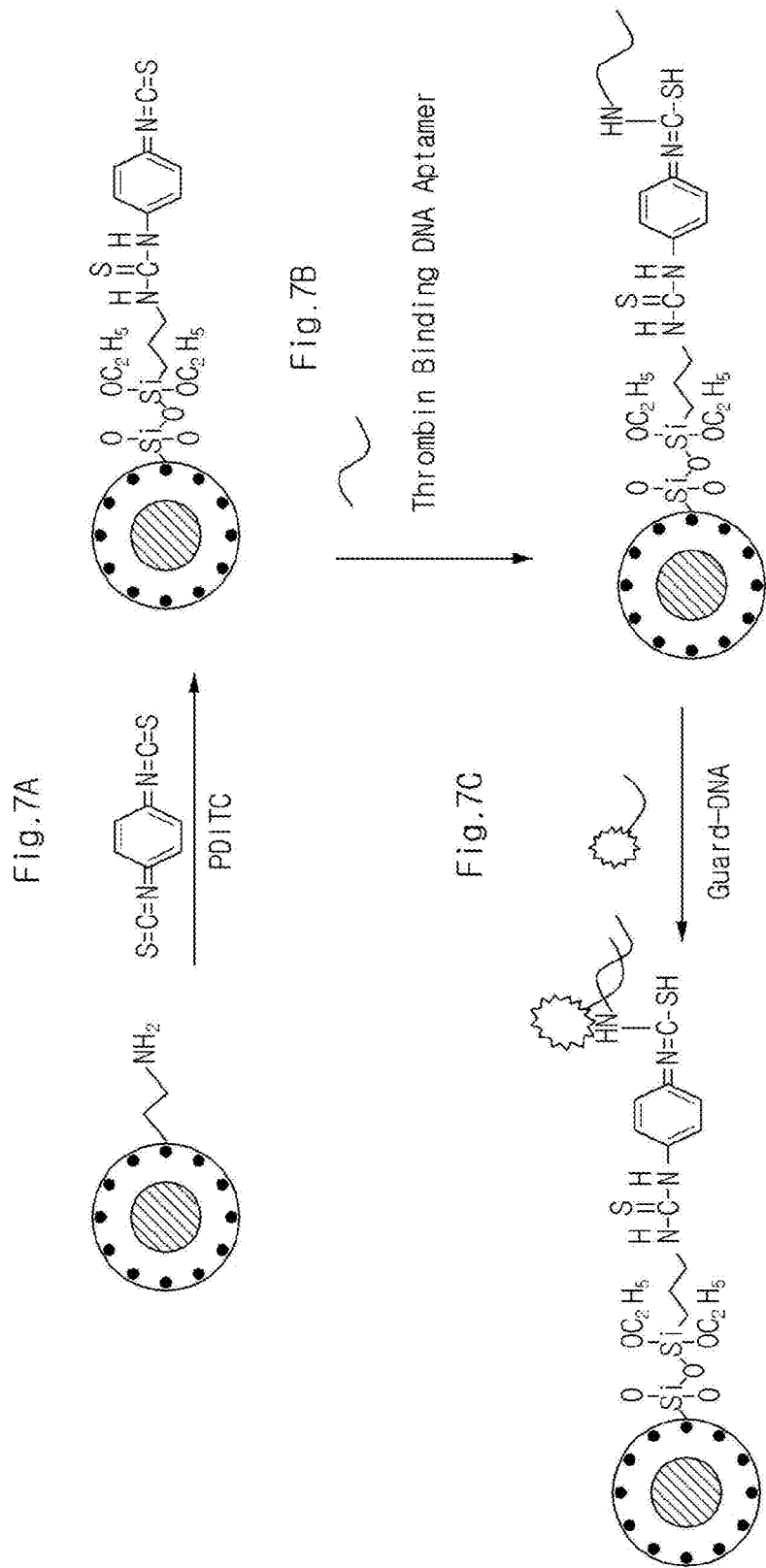

DEVICE AND METHOD FOR DETECTING BIOMOLECULE

CROSS-REFERENCE TO RELATED APPLICATIONS

This application claims priority under 35 U.S.C. §119 to Korean Patent Applications No. 10-2011-0091957, filed on Sep. 9, 2011 and No. 10-2011-0075663, filed on Jul. 29, 2011 in the Korean Intellectual Property Office, the disclosure of which is incorporated herein by reference in its entirety.

BACKGROUND

1. Field

The present disclosure relates to a device and a method for detecting a biomolecule using a nucleic acid aptamer.

2. Description of the Related Art

Aptamers are single-stranded DNA or RNA molecules isolated and obtained from oligomers that bind to a specific chemical or biological molecule with high affinity and selectivity. They have been used for detection of biomolecules. Since the aptamers are based on oligonucleotides, they have many advantages over protein-based antibodies. That is to say, they can be obtained ex vivo and a variety of organic and inorganic substances may be used as target molecules. In addition, once a specific aptamer binding specifically to a specific target molecule is identified, it can be produced in large scale at low cost.

However, although the aptamer can recognize the target molecule, it cannot provide signals reporting the binding with the target molecule. Thus, it is needed to develop a method for complementing these properties of the aptamer and maximizing its function as a probe molecule.

A method of using a cantilever for detecting biomolecules has been developed (Korean Patent Publication No. 10-2011-0055930). In this method, a cantilever sensor and a DNA aptamer immobilized on the cantilever are used to detect thrombin. Therefore, a method allowing for convenient detection of a biomolecule using an aptamer without using the cantilever is needed.

Although quantum dot was discovered in the 1970s, it has been used in the field of life science for only 4-5 years. A quantum dot consisting of a CdSe core and a ZnS shell is a spherical material with a diameter ranging from several nanometers to tens of nanometers. Since it emits fluorescence of different wavelength according to the particle size, the quantum dot can be utilized variously in basic life sciences such as cell biology as well as in applied life sciences such as protein chips and biosensors. The quantum dot is excitable with light of various wavelengths from UV to red light and has a narrow, adjustable emission spectrum. Being an inorganic material, it is stable against chemical reactions and can be easily bound to a biomaterial through surface treatment. In addition, since the quantum dot has superior optical stability and can be monitored continuously in real time, it is an attractive material in the field of biosensors. However, its use in biosensors has been limited since the quantum yield of light emission decreases significantly when the quantum dot is changed from the hydrophobic form to the hydrophilic form or when it is included in other materials.

A method of detecting multiple proteins by immobilizing aptamers for the target proteins on quantum dots with different emission values was developed (Matthew et al. *Chem Bio Chem* 2005, 6, 2163-2166). This method is problematic in that quantification of the detected proteins is difficult, a high-sensitivity fluorescence detector is required for detection of fluorescence, and an accurate control of the flow channel is necessary. In addition, the analysis time tends to be long and a large amount of sample is needed.

Also, there was developed an aptamer-based sandwich analysis method based on sandwich ELISA for quantification (Yolanda et al. *Anal. Chem.* 2010, 82, 5591-5597) and fluorescence analysis using aptamers for detection of proteins. This method is problematic in that the analysis protocol is very complicated and two or more epitopes are required for the target protein.

SUMMARY

The present disclosure is directed to providing a method and a device for detecting a biomolecule allowing for more effective and simple detection of a biomolecule in a sample.

In one general aspect, the present disclosure provides a method for detecting a biomolecule including: immobilizing a nucleic acid aptamer capable of specifically binding to a biomolecule to be detected on the surface of a bead on which fluorophores are arranged; hybridizing the nucleic acid aptamer with a guard nucleic acid (g-nucleic acid) labeled with a quencher to quench fluorescence; and reacting a sample including the biomolecule to be detected with the nucleic acid aptamer and detecting a fluorescence signal emitted as the biomolecule binds with the nucleic acid aptamer and the g-nucleic acid labeled with the quencher is separated.

In an exemplary embodiment of the present disclosure, the bead may include: a magnetic core; porous beads surrounding the core; and fluorophores arranged on the surface of the porous beads.

In an exemplary embodiment of the present disclosure, in the step of detecting the fluorescence signal, the fluorescence signal may be detected by fixing the magnetic bead in a magnetophoresis zone formed by arranging magnets on a microfluidic device.

In an exemplary embodiment of the present disclosure, the magnetic bead may further include a porous layer surrounding the surface of the porous beads on which the fluorophores are arranged.

In an exemplary embodiment of the present disclosure, the porous bead may be made of at least one selected from a group consisting of silica, titania, zirconia and zeolite.

In an exemplary embodiment of the present disclosure, the fluorophore may be selected from a group consisting of quantum dot, fluorescein, tetramethylrhodamine, Cy 5, Cy 3 and Texas Red.

In an exemplary embodiment of the present disclosure, the quencher may be dabcyl or black hole quencher.

In an exemplary embodiment of the present disclosure, the biomolecule may be selected from a group consisting of DNA, RNA, antibody, ligand, receptor, natural compound, synthetic peptide, protein, bacteria, virus and cell.

In an exemplary embodiment of the present disclosure, the nucleic acid aptamer may be selected from a group consisting of DNA aptamer, RNA aptamer and modified RNA aptamer.

In an exemplary embodiment of the present disclosure, the g-nucleic acid may be selected from a group consisting of g-DNA, g-RNA and g-PNA.

In another general aspect, the present disclosure provides a device for detecting a biomolecule for conducting the method for detecting a biomolecule, which includes: a substrate comprising a microchannel; and magnets arranged on the substrate.

In an exemplary embodiment of the present disclosure, the device for detecting a biomolecule may have a buffer inlet, a sample inlet and an outlet.

Apparatus and method for detecting biomolecule according to the present disclosure may allow for effective, convenient and fast detection of the biomolecule to be detected, enable quantitative analysis, and enable detection of even a trace amount of sample. Furthermore, the cost of analysis may be minimized by using minimized sample in analysis.

BRIEF DESCRIPTION OF THE DRAWINGS

The above and other objects, features and advantages of the present disclosure will become apparent from the following description of certain exemplary embodiments given in conjunction with the accompanying drawings, in which:

FIG. 5A, 5B, 5C show detection of thrombin using a magnetic bead of the present disclosure;

FIG. 7A, 7B, 7C show a procedure of immobilizing a DNA aptamer on a magnetic bead and hybridizing a g-DNA labeled with a quencher with the DNA aptamer;

DETAILED DESCRIPTION OF MAIN ELEMENTS

| | |
|---|---|
| 10: buffer inlet | 20: sample inlet |
| 30: outlet | 40: magnet |
| 100: substrate | 110: first substrate |
| 120: second substrate | 200: microchannel |
| 300: magnetic bead | 310: magnetic core |
| 320: fluorophore | 330: porous bead |
| 400: nucleic acid aptamer | 500: g-nucleic acid |
| 510: quencher | |

DETAILED DESCRIPTION

Hereinafter, exemplary embodiments will be described in detail with reference to the accompanying drawings.

Figure 1:
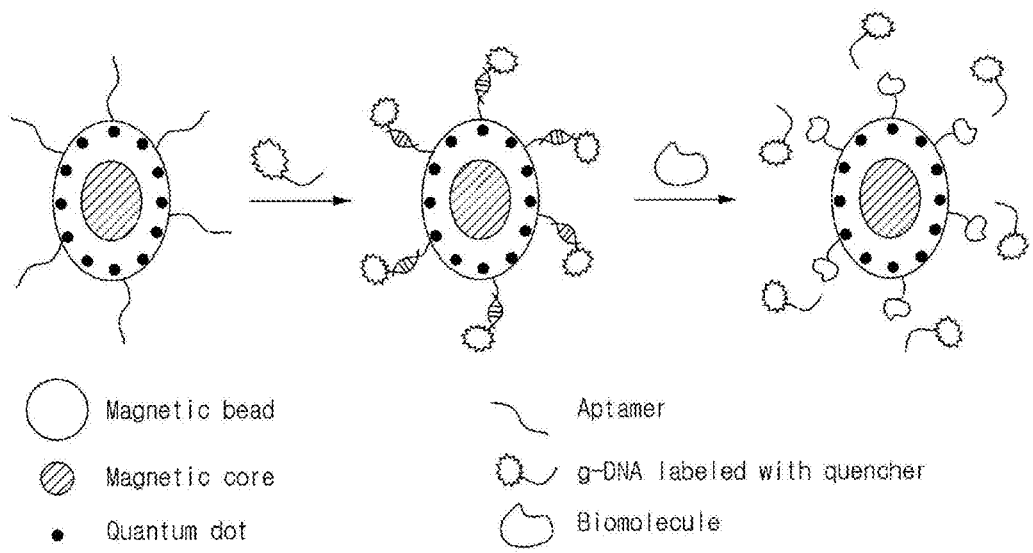
FIG. 1A, 1B, 1C show a procedure of detecting a biomolecule using a magnetic bead on which a guard nucleic acid (g-nucleic acid) labeled with a quencher is hybridized with a nucleic acid aptamer, wherein FIG. 1A the nucleic acid aptamer is immobilized on the surface of the bead on which fluorophores are arranged, FIG. 1B the g-nucleic acid labeled with the quencher is hybridized with the nucleic acid aptamer to quench fluorescence, and FIG. 1C a biomolecule is reacted with the nucleic acid aptamer, so that the g-nucleic acid labeled with the quencher is separated and fluorescence is recovered.

The present disclosure provides a method for detecting a biomolecule comprising: immobilizing a nucleic acid aptamer capable of specifically binding to a biomolecule to be detected on the surface of a bead on which fluorophores are arranged (FIG. 1A); hybridizing the nucleic acid aptamer with a guard nucleic acid (g-nucleic acid) labeled with a quencher to quench fluorescence (FIG. 1B); and reacting a sample including the biomolecule to be detected with the nucleic acid aptamer and detecting a fluorescence signal emitted as the biomolecule binds with the nucleic acid aptamer and the g-nucleic acid labeled with the quencher is separated (FIG. 1C).

The fluorophores may be arranged on the surface of the bead through self-assembly. Self-assembly refers to a process in which the fluorophores are spontaneously arranged on the surface of the bead with a predetermined pattern. Specifically, the fluorophores may be distributed on the surface of the bead. It is because, if the fluorophores are distributed deep inside the bead, the intensity of absorption or emission of light becomes too weak.

The bead may be specifically a magnetic bead, more specifically one comprising: a magnetic core; porous beads surrounding the core; and fluorophores arranged on the surface of the porous beads. Also, the magnetic bead may further comprise a porous layer surrounding the surface of the porous beads on which the fluorophores are arranged. To take an example wherein the fluorophore is a quantum dot, the quantum dots distributed on the surface of the porous beads may have a short life cycle and stability may decrease if the quantum dots bind directly to the biomolecule. By providing the porous layer surrounding the surface of the porous beads, the stability may be improved.

The porous bead may be made of an inorganic material having a high refractive index. For example, it may be made of at least one selected from a group consisting of silica, titania, zirconia and zeolite, specifically silica.

Figure 2:
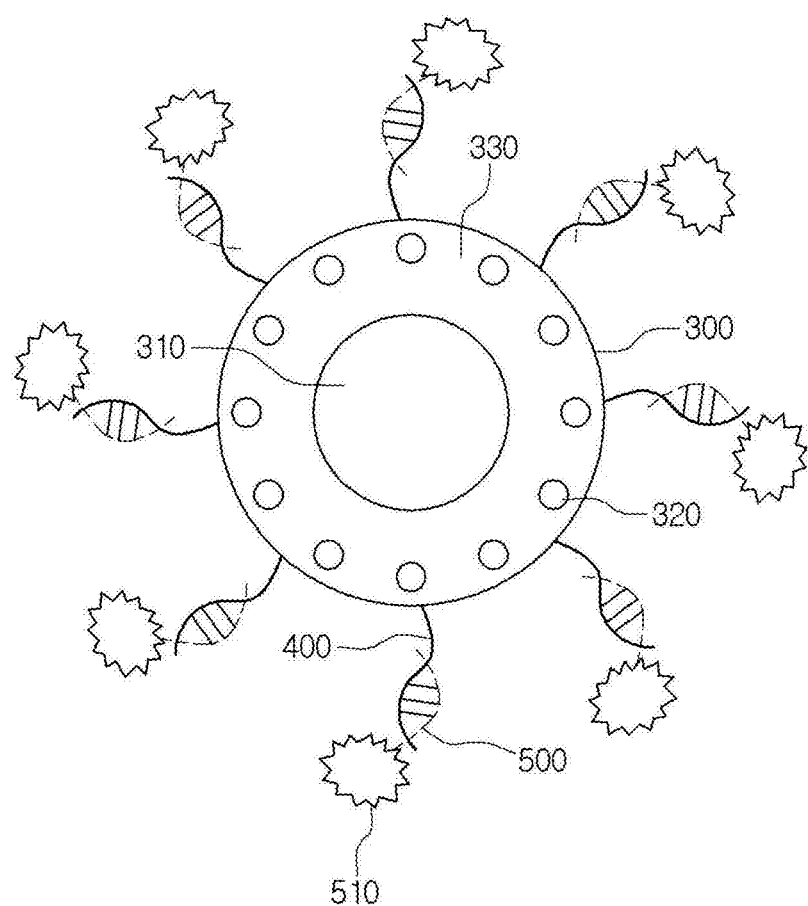
FIG. 2 shows a nucleic acid aptamer immobilized on the surface of a magnetic bead on which fluorophores are arranged, the nucleic acid aptamer being hybridized with a g-nucleic acid labeled with a quencher to quench fluorescence.

FIG. 2 shows an example wherein a nucleic acid aptamer is immobilized on the surface of a magnetic bead on which fluorophores are arranged and the nucleic acid aptamer is hybridized with a g-nucleic acid labeled with a quencher to quench fluorescence. In FIG. 2, the magnetic bead 300 comprises: a magnetic core 310; porous beads 330 surrounding the core; fluorophores 320 arranged on the surface of the porous beads. In addition, the magnetic bead further comprises a porous layer(not appeared in FIG. 2) surrounding the surface of the porous beads on which the fluorophores are arranged. A nucleic acid aptamer 400 is immobilized on the magnetic bead and a g-nucleic acid 500 labeled with a quencher 510 is hybridized with the nucleic acid aptamer 400, such that the quencher 510 quenches fluorescence emitted by the fluorophore 320.

The fluorophore may be any fluorophore known to those skilled in the art. For example, one selected from a group consisting of quantum dot, fluorescein, tetramethylrhodamine, Cy 5, Cy 3 and Texas Red may be used. Specifically, quantum dot may be used.

A quantum dot is a nanosized semiconductor crystalline particle, comprising a group II-IV semiconductor (e.g., CdSe, CdTe, CdS, etc.) as a core. As excited electrons return from the conduction band to the valence band, fluorescence is emitted. The fluorescence wavelength depends on the particle size of the quantum dot, one having a smaller particle size emitting fluorescence of shorter wavelength. Therefore, fluorescence of almost all wavelength regions can be emitted by controlling the particle size. In an exemplary embodiment of the present disclosure, the emission wavelength may be controlled by controlling the size of the quantum dot and a quencher absorbing the emitted fluorescence may be selected for use.

The biomolecule to be detected may be any one specifically binding to a specific nucleic acid aptamer and is not particularly limited. For example, it may be DNA, RNA, antibody, ligand, receptor, natural compound, synthetic peptide, protein, bacteria, virus or cell.

As used herein, the term "nucleic acid aptamer" includes all single-stranded oligonucleotides, having a size of about 10-90 nucleotides, various 3-dimensional structures and high affinity for specific substances. The nucleic acid aptamer binds to a target biomolecule in a cell and inhibits its function.

The nucleic acid aptamer may be selected from a group consisting of a DNA aptamer, an RNA aptamer and a modified RNA aptamer.

In the present disclosure, the g-nucleic acid refers to a single-stranded nucleic acid molecule complementary to the terminal portion of the nucleic acid aptamer and an extension thereof. In an exemplary embodiment of the present disclosure, the g-nucleic acid has a sequence capable of specifically binding to the biomolecule. The g-nucleic acid may be selected from a group consisting of a guard deoxyribonucleic acid (g-DNA), a guard ribonucleic acid (g-RNA) and a guard peptide nucleic acid (g-PNA).

Figure 3:
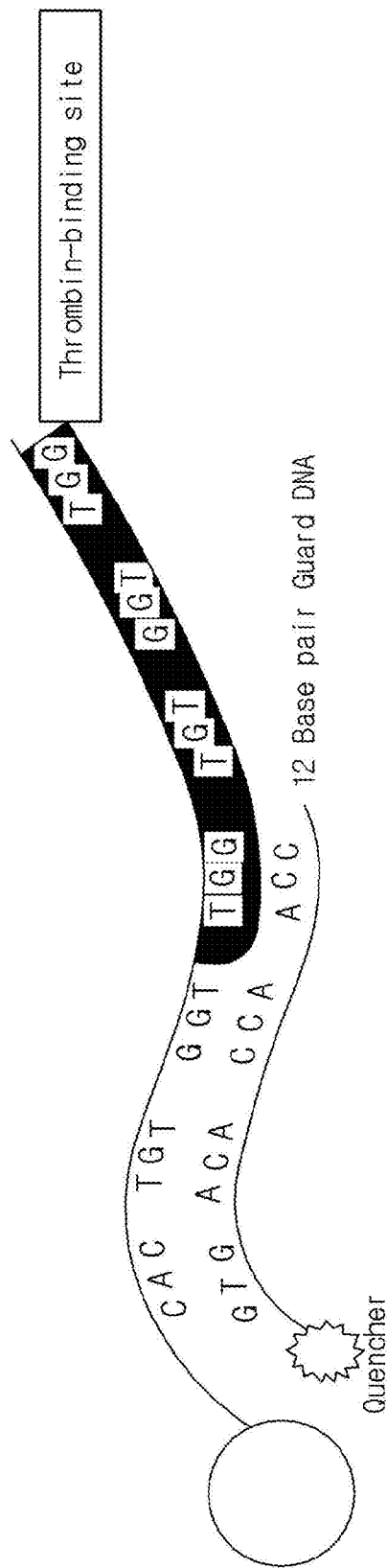
FIG. 3 shows a DNA aptamer-g-DNA duplex in which a DNA aptamer is hybridized with a g-DNA, wherein a quencher is labeled at the end of the g-DNA.

The quencher may be any material capable of reducing the intensity of fluorescence (photoluminescence). For example, dabcyl or black hole quencher may be used. The quencher may be bound at the terminal, specifically at the 5'-terminal or 3'-terminal, of the g-nucleic acid. Referring to FIG. 3, a g-DNA is labeled with a quencher at its terminal.

Figure 4A:
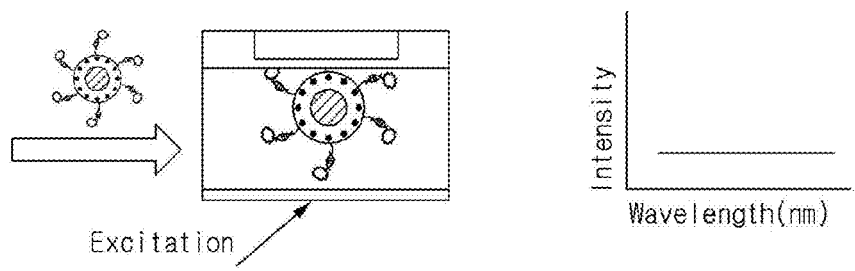
FIG. 4A, 4B show change in photoluminescence (PL) intensity of thrombin detected with a magnetic bead on which a g-DNA labeled with a quencher is hybridized with a DNA aptamer.
Figure 4B:
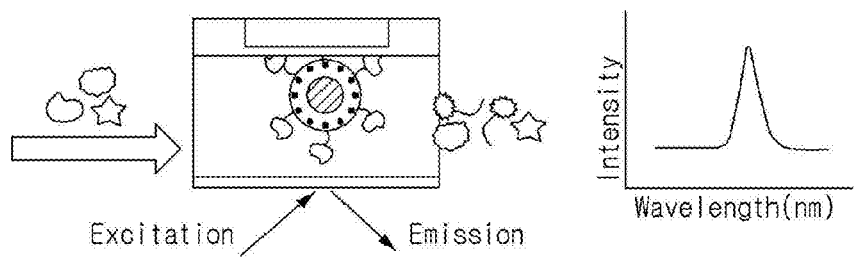

The quencher is labeled at the g-nucleic acid which is hybridized with the nucleic acid aptamer immobilized on the magnetic bead and quenches fluorescence from the fluorophores arranged on the surface of the magnetic bead. Referring to FIG. 4A, a magnetic bead is provided in a magnetic zone formed by a magnet inside a microchannel, and a g-DNA labeled with a quencher is hybridized with a DNA aptamer and immobilized on the magnetic bead. From the measurement of photoluminescence intensity, it can be seen that fluorescence is not emitted. Referring to FIG. 5A, it can be seen that fluorescence is emitted before hybridization with a g-DNA labeled with a quencher. And, referring to FIG. 5B, it can be seen that the fluorescence is quenched after the g-DNA labeled with the quencher binds to a DNA aptamer. When a quantum dot is used as the fluorophore, a quencher capable of absorbing the light of a specific wavelength emitted from the quantum dot may be used. When the nucleic acid aptamer reacts with a biomolecule reacting specifically therewith, the g-nucleic acid that has been is hybridized with the nucleic acid aptamer is separated and the quencher that has been bound to the g-nucleic acid is also separated. Then, the fluorescence that has been quenched by the quencher is recovered and emitted again. Referring to FIG. 4B and FIG. 5C, it can be seen that the fluorescence is recovered and emitted.

Referring to FIG. 5C, it can be seen that fluorescence is recovered within 5 minutes in an exemplary experiment. As such, since the detection method according to the present disclosure allows for confirmation of detection in real time, a fast and convenient detection is possible. It is because the fluorophores are arranged on the whole surface of the bead and the nucleic acid aptamer bound to the bead surface allows for detection of the specific biomolecule on the whole surface of the bead. Consequently, fast response resulting from the large detection surface area allows for confirmation of detection in real time.

In the detection method of the present disclosure, the step of detecting the fluorescence signal may further comprise a step of fixing the magnetic bead in a magnetophoresis zone formed by arranging magnets on a microfluidic device and detecting the fluorescence signal. The microfluidic device may be one comprising a channel through which a microfluid can flow and magnets may be arranged on the microfluidic device.

The fluorescence signal may be detected using a fluorescence detector. Referring to FIG. 4A, 4B and FIG. 5A, 5B, 5C it can be seen that fluorescence is recovered and emitted after reaction with the biomolecule reacting specifically with the DNA aptamer.

The detection method according to the present disclosure is advantageous in that analysis is much simpler than the method without magnets being arranged since one has only to read the fluorescence signal from the magnetophoresis zone in which the magnets are arranged. It is because the magnetic bead is fixed in the magnetophoresis zone formed by the magnets and reaction between the biomolecule and the nucleic acid aptamer occurs in the magnetophoresis zone. In addition, quantitative analysis is possible by arranging a predetermined amount of the beads in the magnetophoresis zone.

Figure 6A:
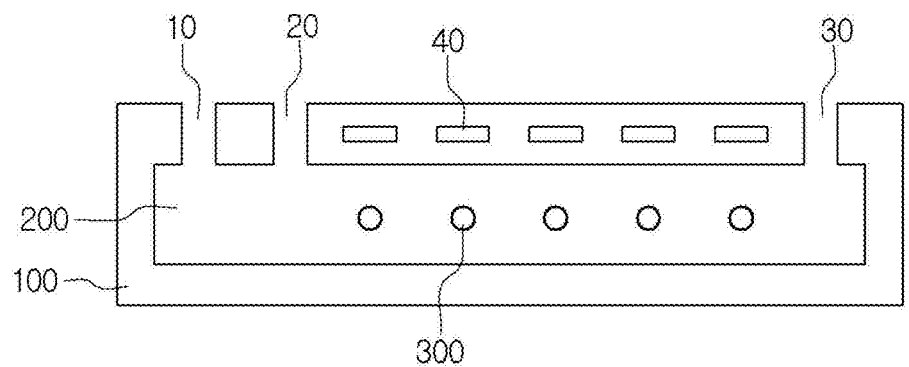
FIG. 6A, 6B show cross-sectional views of devices for detecting a biomolecule according to exemplary embodiments of the present disclosure.
Figure 6B:
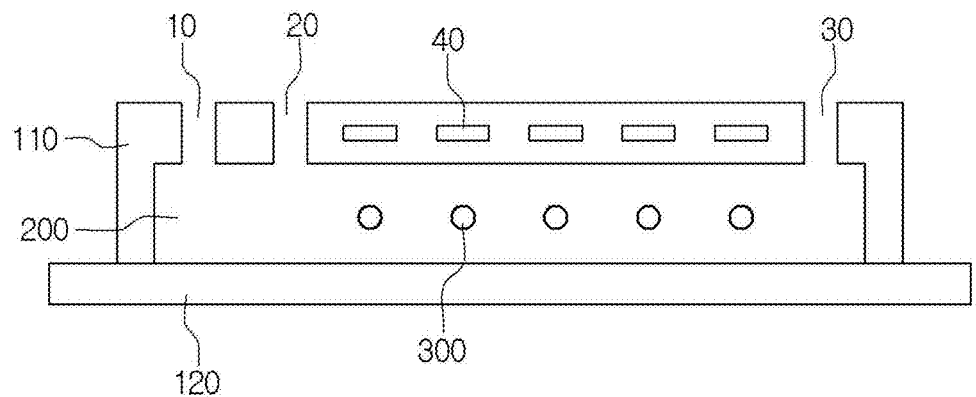
Figure 8:
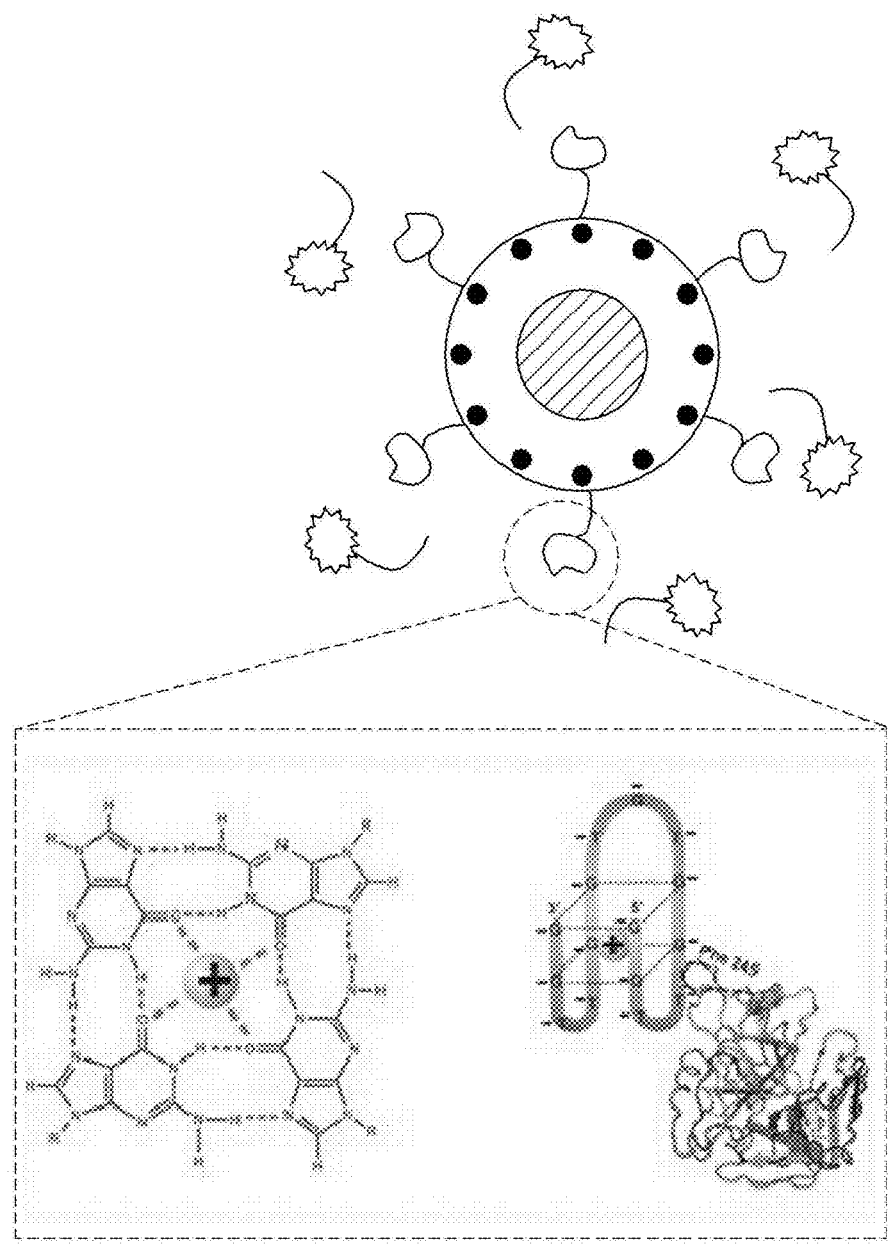
FIG. 8 shows a DNA aptamer immobilized on the surface of a magnetic bead bound to thrombin.

The present disclosure also provides a device for detecting a biomolecule for conducting the method for detecting a biomolecule, which comprises: a substrate comprising a microchannel; and magnets arranged on the substrate. Exemplary embodiments of the device for detecting a biomolecule are shown in FIG. 6A, 6B. The detection device comprises: a substrate 100 comprising a microchannel 200; and magnets 40 arranged on the substrate. It also comprises a buffer inlet 10, a sample inlet 20 and an outlet 30 formed on the substrate. FIG. 6A shows an example wherein the substrate 100 is formed integrally, and the magnets 40 are arranged with predetermined intervals on the microchannel 200 on one side of the substrate. FIG. 6B shows an example wherein a first substrate 110 and a second substrate 120 are coupled to form the substrate, and the magnets 40 are arranged with predetermined intervals on one of the first substrate 110 and the second substrate 120.

The substrate may be made of one selected from, for example, a group consisting of silicon wafer, glass, quartz, metal and plastic. Specifically, the plastic may be selected from a group consisting of cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA) and polydimethylsiloxane (PDMS).

Figure 10:
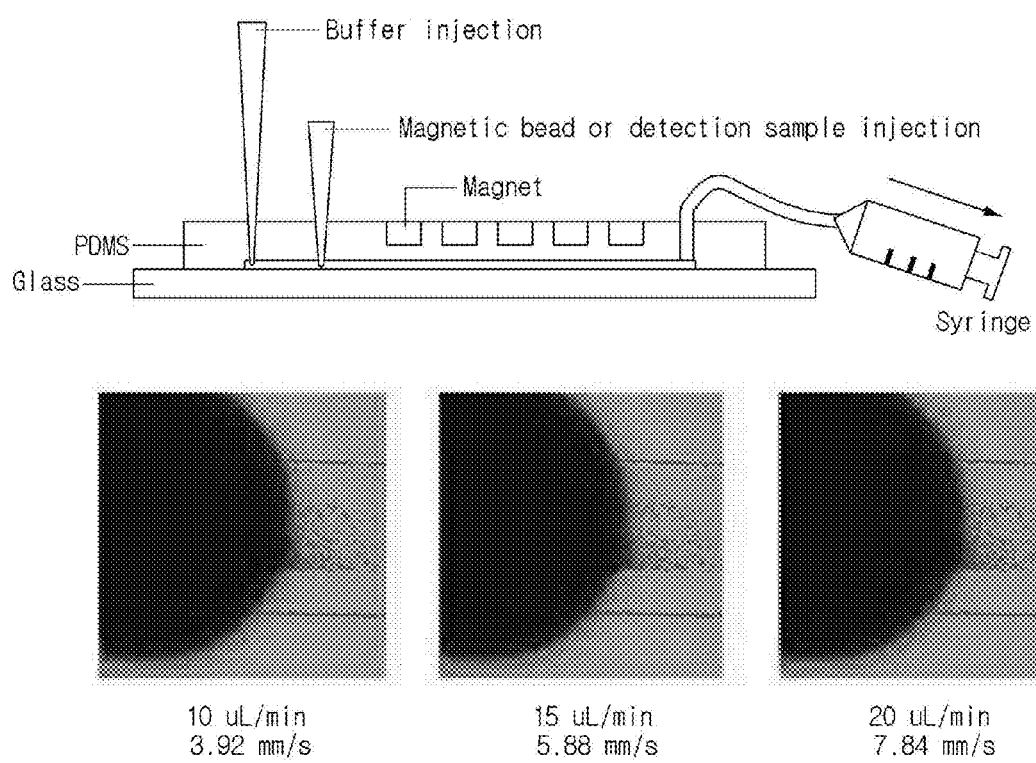
FIG. 10 shows a procedure of manufacturing a device for detecting a biomolecule, injecting a buffer and a magnetic bead in a microchannel, and controlling the flow rate of the magnetic bead in the channel by varying flow volume.

A buffer may be injected into the microchannel through the buffer inlet 10, and the magnetic bead and a sample containing the biomolecule to be detected may be injected into the microchannel through the sample inlet 20. The outlet 30 may be connected with a syringe so as to discharge the sample and buffer excluding the specific biomolecule desired to be detected, the g-nucleic acid labeled with the quencher separated after the reaction of the biomolecule with the nucleic acid aptamer, or the like. This example is illustrated in FIG. 10.

The examples will now be described. The following examples are for illustrative purposes only and those skilled in the art will appreciate that the scope of this disclosure is not limited by the following examples.

EXAMPLE 1

Immobilization of DNA Aptamer on Surface of Magnetic Bead and Hybridization with g-DNA Labeled with Quencher A thrombin-binding DNA aptamer was immobilized on the surface of a magnetic bead on which quantum dots are arranged and then a g-DNA labeled with a quencher was hybridized with the aptamer. The magnetic bead with the DNA aptamer attached is shown in FIG. 2 and a procedure of preparing the same is shown in FIG. 7A, 7B, 7C. Referring to FIG. 7A 4-phenylene diisothiocyanate (PDITC) was dissolved in N,N-dimethylformamide (DMF) and reacted with a magnetic bead having a propylamine group at 25° C. for 2 hours, FIG. 7B the amine group was modified so that isothiocyanate can bind to the magnetic bead, and the magnetic bead was reacted with a thrombin-binding aptamer diluted in 10 μM 1× PBS for 2 hours at room temperature, and FIG. 7C the magnetic bead was reacted with a DNA labeled with the quencher Iowa Black RQ, diluted in hybridization buffer (Tris-HCl 20 mM, $MgCl_2$ 20 mM), for 1 hour.

Since the magnetic bead is excited at 450 nm and emits light at 610 nm, Iowa Black RQ absorbing light with wavelength of 500-700 nm was used as the quencher.

Thus prepared DNA aptamer-g-DNA duplex comprises a 5'-extended thrombin-binding DNA aptamer [21-mer: 5'-CAC TGT GGT TGG TGT GGT TGG-3': SEQ ID NO: 1; The sequence 5'-GGT TGG TGT GGT TGG-3' is the thrombin-binding sequence (SEQ ID NO: 2).] and a g-DNA (5'-CCA ACC ACA GTG-3': SEQ ID NO: 3) (see FIG. 3, FIG. 5A, 5B, 5C and FIG. 8).

EXAMPLE 2

Injection of Thrombin and Measurement of Fluorescence

10 μg/ml thrombin was injected into a microchannel as a target substance through a sample inlet 20. After reaction with the magnetic bead, it was observed under a microscope that the dark portion turned red. As seem from FIG. 5A, 5B, 5C, photoluminescence intensity increased within 5 minutes after the injection of thrombin.

FIG. 5A, 5B, 5C show the detection images of thrombin using the magnetic bead with the quantum dots attached. FIG. 5A shows the magnetic bead with the nucleic acid aptamer immobilized thereon, FIG. 5B shows the magnetic bead hybridized with the g-DNA, and FIG. 5C shows the fluorescence images after reaction with thrombin.

When light with wavelength of 500-700 nm was irradiated, no fluorescence signal was emitted from the quantum dot.

Figure 9:
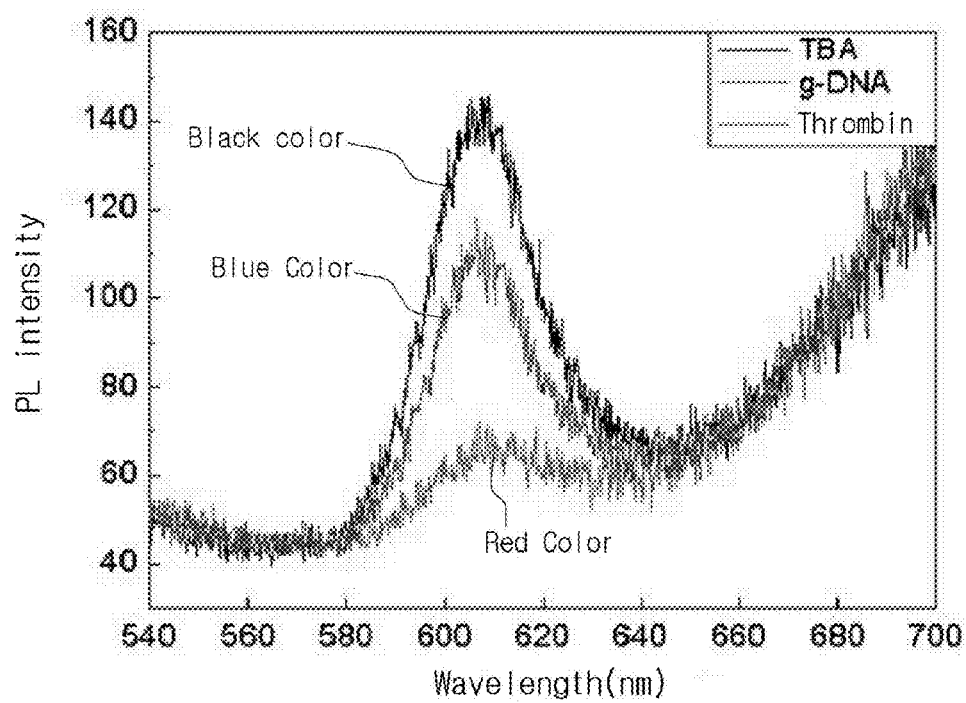
FIG. 9 shows change in PL intensity measured by a method for detection of the present disclosure (TBA: thrombin-binding DNA aptamer)

When the aptamer was bound to thrombin, the g-DNA labeled with the quencher was separated from the aptamer and discharged through the channel. As a result, a fluorescence signal was observed at 610 nm, which is the emission wavelength of the quantum dot (FIG. 9).

EXAMPLE 3

Fabrication of Detection Device

In order to detect the fluorescence recovered as the biomolecule to be detected reacted with the DNA aptamer, a device for detecting a biomolecule was fabricated (FIG. 10). A long, linear microfluidic channel was prepared with a dimension of 500 μm (width)×85 μm (height)×40 mm (length). A magnetic zone for capturing the magnetic bead was prepared by arranging magnets at one side of the channel. The flow volume was set at 10-20 μL/min to adjust the average bead flow rate to 3.91-7.84 mm/s.

The method and device for detecting a biomolecule according to the present disclosure allow for effective, convenient and fast detection of the biomolecule to be detected, enable quantitative analysis, and enable detection of even a trace amount of sample. In addition, cost of analysis is minimized since only a small amount of sample is required.

While the present disclosure has been described with respect to the specific embodiments, it will be apparent to those skilled in the art that various changes and modifications may be made without departing from the spirit and scope of the disclosure as defined in the following claims.

What is claimed is:

1. A method for detecting a biomolecule comprising:
   immobilizing a nucleic acid aptamer on the surface of a bead on which quantum dots are arranged that is capable of specifically binding to a protein to be detected;
   hybridizing the nucleic acid aptamer with a guard nucleic acid (g-nucleic acid) labeled with a quencher to quench fluorescence; and
   reacting a sample including the protein to be detected with the nucleic acid aptamer and detecting a fluorescence signal emitted as the protein binds with the nucleic acid aptamer and the g-nucleic acid labeled with the quencher is separated;
   wherein the bead is a magnetic bead comprising: a magnetic core; porous beads surrounding the core; and quantum dots arranged on the surface of the porous beads.

2. The method for detecting a biomolecule according to claim 1, wherein, in said detecting the fluorescence signal, the fluorescence signal is detected by fixing the magnetic bead in a magnetophoresis zone formed by arranging magnets on a microfluidic device.

3. The method for detecting a biomolecule according to claim 2, wherein the magnetic bead further comprises a porous layer surrounding the surface of the porous beads on which the quantum dots are arranged.

4. The method for detecting a biomolecule according to claim 2, wherein the porous bead is made of at least one selected from a group consisting of silica, titania, zirconia and zeolite.

5. The method for detecting a biomolecule according to claim 1, wherein the quencher is dabcyl or black hole quencher.

6. The method for detecting a biomolecule according to claim 1, wherein the nucleic acid aptamer is selected from a group consisting of DNA aptamer, RNA aptamer and modified RNA aptamer.

7. The method for detecting a biomolecule according to claim 1, wherein the g-nucleic acid is selected from a group consisting of g-DNA, g-RNA and g-PNA.

\* \* \* \* \*